US010198553B2

(12) United States Patent
Hurd et al.

(10) Patent No.: US 10,198,553 B2
(45) Date of Patent: Feb. 5, 2019

(54) COMBINED CGH AND ALLELE SPECIFIC HYBRIDISATION METHOD

(71) Applicant: Oxford Gene Technology IP Ltd., Oxfordshire (GB)

(72) Inventors: Douglas Hurd, Oxfordshire (GB); Edwin Southern, Oxfordshire (GB)

(73) Assignee: OXFORD GENE TECHNOLOGY (OPERATIONS) LTD., Oxfordshire (GB)

( * ) Notice: Subject to any disclaimer, the term of this patent is extended or adjusted under 35 U.S.C. 154(b) by 45 days.

(21) Appl. No.: 15/412,504

(22) Filed: Jan. 23, 2017

(65) Prior Publication Data
US 2017/0154152 A1 Jun. 1, 2017

Related U.S. Application Data

(62) Division of application No. 13/520,935, filed as application No. PCT/GB2011/000012 on Jan. 7, 2011, now Pat. No. 9,587,278.

(30) Foreign Application Priority Data

Jan. 8, 2010 (GB) .................................. 1000315.0
Apr. 16, 2010 (GB) .................................. 1006438.4
Aug. 25, 2010 (GB) .................................. 1014226.3

(51) Int. Cl.
*C12Q 1/68* (2018.01)
*G06F 19/20* (2011.01)
*C12Q 1/6837* (2018.01)
*C12Q 1/6886* (2018.01)
*C12Q 1/6883* (2018.01)

(52) U.S. Cl.
CPC .......... *G06F 19/20* (2013.01); *C12Q 1/6837* (2013.01); *C12Q 1/6883* (2013.01); *C12Q 1/6886* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| 9,587,278 | B2* | 3/2017 | Hurd .................... C12Q 1/6837 |
| 2003/0207278 | A1 | 11/2003 | Khan et al. |
| 2006/0160105 | A1* | 7/2006 | Dhallan ............... C12Q 1/6827 435/6.16 |
| 2006/0173635 | A1 | 8/2006 | Yakhini et al. |
| 2006/0263777 | A1* | 11/2006 | Tong .......................... G01J 3/42 435/6.12 |
| 2007/0238106 | A1 | 10/2007 | Barrett et al. |
| 2008/0052789 | A1* | 2/2008 | Jorgensen .......... C12N 15/8243 800/278 |
| 2008/0070792 | A1* | 3/2008 | Stoughton ............ C12Q 1/6883 506/9 |
| 2008/0233117 | A1* | 9/2008 | Roberts ................ C07K 16/303 424/133.1 |
| 2008/0240543 | A1* | 10/2008 | Budach .............. G01N 21/4788 382/141 |
| 2008/0274543 | A1* | 11/2008 | Philipp .................... C12N 5/00 435/353 |
| 2009/0061436 | A1* | 3/2009 | Weber .............. G01N 33/57484 435/6.14 |

FOREIGN PATENT DOCUMENTS

GB 2 452 437 3/2009
WO 2007/131135 11/2007

OTHER PUBLICATIONS

International Search Report dated Apr. 20, 2011, in International (PCT) Application No. PCT/GB2011/000012.
Search Report dated May 7, 2010, in corresponding UK Patent Application No. GB1000315.0.
K. Lo et al., "Comprehensive Analysis of Loss of Heterozygosity Events in Glioblastoma Using the 100K SNP Mapping Arrays and Comparison with Copy Number Abnormalties Defined by BAC Array Comparative Genomic Hybridization", Genes, Chromosomes & Cancer, vol. 47, pp. 221-237, 2008.
J. Cowell et al., "Application of Oligonucleotides Arrays for Coincident Comparative Genomic Hybridization, Ploidy Status and Loss of Heterozygosity Studies in Human Cancers", Methods in Molecular Biology, Chapter 5, vol. 56, pp. 47-65, 2009.
D. Peiffer et al., "High-resolution genomic profiling of chromosomal aberrations using Infinium whole-genome genotyping", Genome Research, vol. 16, pp. 1136-1148, 2006.
International Preliminary Report on Patentability and Written Opinion dated Apr. 20, 2011, in International (PCT) Application No. PCT/GB2011/000012.

(Continued)

*Primary Examiner* — James Martinell
(74) *Attorney, Agent, or Firm* — Wenderoth, Lind & Ponack, L.L.P.

(57) ABSTRACT

The invention combines the fields of comparative genomic hybridization (CGH) analysis and SNP array analysis. It relates to methods for detecting and mapping genetic abnormalities associated with various diseases. In particular the invention provides a method for simultaneously performing array CGH and SNP array analysis on a genomic DNA sample comprising contacting a nucleic acid array which comprises a first probe set and a second probe set with a genomic DNA sample, comprising a test and reference sample, under hybridization conditions, comparing the amount of test sample and reference sample hybridized to the hybridization probes of the first probe set, comparing the amount of test sample and reference sample hybridized to the hybridization probes of the second probe set; and using the data obtained to determine the copy number of at least one locus; and at least one SNP in the genomic DNA sample.

6 Claims, 6 Drawing Sheets

(56) References Cited

OTHER PUBLICATIONS

Davies et al, "Array CGH technologies and their applications to cancer genomes", Chromosome Research, vol. 13, pp. 237-248, 2005.

McCarroll et al., "Integrated detection and population-genetic analysis of SNPs and copy number variation", Nature Genetics, vol. 40, No. 10, pp. 1166-1174, 2008.

* cited by examiner

COMBINED CGH AND ALLELE SPECIFIC HYBRIDISATION METHOD

This application claims the benefit of United Kingdom patent applications 1000315.0 (filed 8 Jan. 2010), 1006438.4 (filed 16 Apr. 2010) and 1014226.3 (filed 25 Aug. 2010), the complete contents of all of which are hereby incorporated herein by reference for all purposes.

TECHNICAL FIELD

The invention combines the fields of comparative genomic hybridisation (CGH) analysis and SNP (or other sequence variation) array analysis. It relates to methods for detecting and mapping genetic abnormalities associated with various diseases. It relates to the use of nucleic acid hybridisation methods for simultaneously detecting copy number and SNP (or other sequence variation) information in genomic DNA samples.

BACKGROUND ART

Comparative genomic hybridisation (CGH) is a molecular-cytogenetic method for the analysis of copy number changes (gains/losses) in a subject's DNA. The technique relies on the comparison of two labelled samples by allowing them to hybridise and subsequently looking for regions of differential hybridisation. It has been used particularly in cytogenetic analysis, where it allows the comparison of a genome isolated from a clinical (test) sample (e.g. derived from a cancer patient) with a control (reference) sample in a single hybridisation. It was originally disclosed in reference 1.

Whereas early CGH methods relied on hybridisation to a reference chromosome sample, array-based CGH methods have since been developed [2-4]. In these methods, the reference chromosome is replaced by an array of immobilised nucleic acid probes, with the individual immobilised sequences having known chromosomal locations and covering the genome to a desired degree. By choosing appropriate probes, this method gives the potential to cover any genomic region of interest, and to any desired resolution. Commercial array CGH kits are now available, including Spectral Chip from Perkin Elmer, CytoChip from BlueGnome, and CGH products from Nimblegen.

These two distinct methods are referred to as 'chromosomal CGH' and 'array CGH'.

Copy number variation in humans can result in certain disease types and, although CGH is a powerful tool for analysing copy number changes in a given subject's DNA, it is only able to provide information about unbalanced chromosomal changes. Structural chromosome aberrations such as balanced reciprocal translocations or inversions can not be detected, as they do not change the copy number, nor is it able to detect copy number neutral loss of heterozygosity (LOH) due to uniparental disomy (UPD).

UPD occurs when two copies of a chromosome, or part of a chromosome, are inherited from one parent and no copies from the other parent [5]. When the (two) homologous chromosomes are inherited from one parent, this is called a heterodisomic UPD. Heterodisomy indicates a meiosis I error. When the two (identical) replica copies of a single homolog of a chromosome are inherited, this is called an isodisomic UPD. Isodisomy indicates either a meiosis II error or postzygotic duplication.

Most occurrences of UPD result in no phenotypical anomalies. However, isodisomy can lead to the manifestation of rare recessive disorders, for example Silver-Russell or Prader Willi syndromes.

Determining if UPD has occurred can use single-nucleotide polymorphisms (SNPs) as markers to track the chromosome and determine if LOH has occurred. A SNP is a DNA sequence variation occurring when a single nucleotide—A, T, C, or G—in the genome differs between members of a population. For example, two sequenced DNA fragments from different individuals, AAGCCTA to AAGCTTA, contain a difference in a single nucleotide at a given position. In this case there are two alleles: C and T. Almost all common SNPs have only two variants. Within a population, SNPs can be assigned an allele frequency which indicates the percentage of the population which possess a particular nucleotide residue at the SNP position.

Standard arrays for array CGH are not capable of detecting SNPs. Array CGH typically uses longer oligos and therefore tolerates a higher stringency to achieve an optimal copy number variation result. SNP arrays tend to use shorter oligos under lower stringency and therefore the standard SNP arrays can, in theory, be used to obtain copy number variation (CNV) data, but because they are not typically capable of generating data of a comparable quality to array CGH they are not used for this purpose. Thus, for example, reference 6 used two different arrays for its combined array-CGH and SNP-LOH analysis.

Reference 7 discloses arrays which can be used for both array CGH and SNP analysis. SNPs are detected by allele-specific chain extension of hybridised probes.

It is an object of the invention to provide methods and apparatuses for simultaneous array CGH and SNP array analysis. In particular it is an object of the invention to provide improved ways of distinguishing if LOH at a locus is caused by deletion or isodisomy.

DISCLOSURE OF THE INVENTION

The invention is based on the combination of standard array CGH techniques with SNP (or other sequence variation) array analysis. Despite the difference in hybridisation conditions used for CGH and SNP arrays, the inventors have surprisingly found that CGH and SNP (and other sequence variation) analysis can be performed simultaneously on the same nucleic acid array. Appropriate design and confirmatory empirical screening can provide SNP probes that function under conditions used for standard array CGH, and guidance for the selection of suitable probes is provided herein.

To design a SNP probe for use in the invention, the genomic location and genotype details are obtained from a source such as EMBL or dbSNP (http://www.ebi.ac.uk/embl/ and http://www.ncbi.nlm.nih.gov/projects/SNP/). These data are then filtered for SNPs which exhibit allelic frequencies in the range of 0.4 to 0.6 in order to maximise the number of informative data points represented on the array.

Fifty nucleotides of upstream and downstream flanking sequence from the genome form part of the SNP probe region. Once added the probes are examined for genome wide uniqueness using the BLAST and/or BLAT algorithms. Oligonucleotide probes of a defined length (e.g. sixty nucleotides in length) specific for these SNPs are generated by combining genomic sequence with linker sequences ranging from 0 to 30 nucleotides in length.

The position of the SNP in relation to the remainder of the genomic sequence of the probe is experimentally evaluated and the best performing versions selected for the final design.

In order to focus the effort of the experimental optimisation all SNPs are filtered for allele frequencies, homology scores of the genomic sequences and melting temperature of the probe sequences. Moreover probes representing all 4 possible alleles on both strands of the genomic sequence are evaluated for every single selected SNP.

Accordingly, the invention provides a method for simultaneously performing array CGH and SNP array analysis on a genomic DNA sample comprising: (a) contacting a nucleic acid array which comprises a first probe set and a second probe set with a genomic DNA sample, comprising a test and reference sample, under hybridisation conditions, wherein: (i) the first probe set, for the detection of copy number variation by array CGH, comprises a plurality of hybridisation probes substantially complementary to a plurality of target nucleotide sequences in the nucleic acid sample; and (ii) the second probe set comprises one or more pair(s) of hybridisation probes for a SNP position, wherein the pair(s) of probes differ in sequence such that a nucleic acid target present in the sample can differentially hybridise to the two probes depending on the nucleotide at the SNP position, and a probe's nucleotide at the SNP position is not the 3' terminal nucleotide; (b) comparing the amount of test sample and reference sample hybridised to the hybridisation probes of the first probe set; (c) comparing the amount of test sample and reference sample hybridised to the hybridisation probes of the second probe set; and (d) using the data obtained in steps (b) and (c) to determine the copy number of at least one locus and at least one SNP in the genomic DNA sample.

The invention also provides a method for distinguishing if loss of heterozygosity (LOH) at a locus is caused by chromosomal deletion or isodisomy comprising: (i) simultaneously performing array CGH and SNP array analysis on a genomic DNA sample according to the method of the invention: (ii) using the data obtained from step (d) of part (i) to distinguishing if loss of heterozygosity (LOH) at a locus is caused by chromosomal deletion or isodisomy; wherein, if all of the SNPs located on a particular chromosome or region of a chromosome are identified as homozygous and there is no indication of copy number variation in the same region, then it is likely that the LOH is a consequence of uniparental isodisomy; if the SNPs located in a particular chromosome or region of a chromosome are not all homozygous and there is an indication of copy number variation in that region, then it is likely that the LOH is a consequence of the chromosomal deletion and not from UPD.

The invention also provides a nucleic acid array that, when contacted with a genomic DNA sample under hybridisation conditions, can (i) provide information about the sample relating to the copy number of one or more loci in the genome; and (ii) distinguish between different alleles present at one or more SNP positions in the genome.

Preferably the nucleic acid array comprises a first probe set and a second probe set, wherein (i) the first probe set, for the detection of copy number variation by array CGH, comprises a plurality of hybridisation probes substantially complementary to a plurality of target nucleotide sequences in the genomic DNA sample; and (ii) the second probe set comprises one or more pair(s) of hybridisation probes for a SNP position, wherein the pair(s) of probes differ in sequence such that a nucleic acid target present in the sample can differentially hybridise to the two probes depending on the nucleotide at the SNP position, and a probe's nucleotide at the SNP position is not the 3' terminal nucleotide.

The invention also allows for the detection of heterodisomy as described below.

Preferably the method comprises detecting the amount of the nucleic acid sample bound to the first and second probe set.

Preferably the DNA sample is a human genomic DNA sample.

Genomic DNA Sample

The DNA sample to be analysed is a genomic DNA (gDNA) sample. Analysis will generally be performed on total genomic DNA which, in a eukaryote, includes DNA from the nucleus and other organelles e.g. from the mitochondria.

The invention can be used for comparing all types of DNA, and is particularly suitable for analysing human cells, including cancer cells.

The genomic DNA sample includes DNA from both a test sample (the sample for which information is to be determined) and a reference sample (a sample of known content). DNA in the test sample and the reference sample may be labelled with first and second labels, respectively. The first and second labels should be distinguishable from each other, e.g. they may be different colors such as green, red, blue, etc. Preferably the labels are fluorescent dyes.

Samples for use with the present invention may be prepared using methods known in the art for preparing samples to be analysed by array CGH. Examples of such methods are well known in the art e.g. as known for the Spectral Chip and CytoChip products.

Because the starting material for array CGH procedure is genomic DNA, which is composed of long chromosomal DNA molecules, the sample DNA needs to be shortened before being applied to the array. This is generally achieved by fragmenting the sample DNA. The sample DNA may be fragmented using any suitable method, including but not limited to restriction digestion after amplification or sonication before random prime labelling and amplification. Fragmentation of genomic DNA in a sample can be achieved physically, chemically, or enzymatically. Physical and chemical fragmentation is essentially random, whereas enzymatic fragmentation using restriction enzymes is sequence-specific and repeatable. Thus restriction digestion is a preferred method for fragmenting gDNA in a sample.

If both a test and a reference sample are being assayed, once the samples have been fragmented they are then labelled with distinguishable dyes.

To give useful results in an array CGH method, the array must contain probes that match the fragmented genomic DNA. Every different fragmentation of a genome will give different hybridisable sequences, and so there will be a different optimum set of probes for each of the fragmentations. Thus the best array for analysing a fragmented genome will depend on the precise fragmentation method that was used. The optimisation of probe sets for use in array CGH is well known in the art and optimisation is a routine practice.

For a specific restriction enzyme, in silico digestion can show the fragments that will be produced. This information can be used to design a set of probes that are hybridisable to the restriction fragments and that cover the genome to the desired degree. Moreover, it can be used to design a set of probes that will offer an appropriate level of coverage. Probe design may also involve standard techniques, such as ensuring that probes are essentially unique within a target genome (i.e. that they have essentially no cross-hybridsation potential). If specific regions are of interest then probes may be focused on these regions e.g. on subtelomeres, on specific chromosomes, on specific genes, etc. Probe design may also be restricted by the number of probes that can be included on the chosen array platform.

To provide enough material for hybridisation in array CGH in situations where the sample is limited, the DNA samples can be subjected to amplification. For example, reference 8 established the efficacy of whole genome amplification (WGA) approaches for achieving this goal.

First Probe Set

The first probe set functions as a CGH array and thus contains a plurality of hybridisation probes substantially complementary to a plurality of target nucleotide sequences in the genomic DNA sample. The target nucleotide sequences may, for example, contain specific genes or, be from a chromosomal region suspected of being present at increased or decreased copy number in cells of interest, e.g., tumour cells.

An array of such target sequences could represent locations that sample either continuously, or at discrete points, any desired portion of a genome, including, but not limited to, an entire genome, a single chromosome, or a portion of a chromosome. The number of target nucleotide sequences and the complexity of the nucleic acids in each would determine the density of sampling.

Preferably the first probe set will comprise ten or more hybridisation probes per chromosome, i.e., 20, 30, 40, 50, 100, 150, 200, 250, 300, 500, 1000, 2000, 3000, 5000, 7500, 10000, 15000, 20000, 25000, 30000, 45000, 50000 or more.

Preferably the hybridisation probes of the first probe set are between 50 to 70 nucleotides in length, i.e., 51, 52, 53, 54, 55, 56, 57, 58, 59, 60, 61, 62, 63, 64, 65, 66, 67, 68, 69 or 70. More preferably the hybridisation probes of the second probe set are 60 nucleotides in length. The probes of the first probe set may all be the same length as each other, or they may be different lengths.

Second Probe Set

The second probe set functions to track the chromosome and determine if LOH has occurred. In a preferred embodiment the second probe set functions as a SNP array and comprises one or more pair(s) of hybridisation probes for a SNP position, wherein the pair(s) of probes differ in sequence such that a nucleic acid target present in the sample can differentially hybridise to the two probes depending on the nucleotide at the SNP position.

The inventors have empirically tested a large number of probes following the methodology described above and found that SNP probes suitable for use under standard array CGH conditions are generally between 50-70 nucleotides in length, e.g. 60 nucleotides in length.

The probes of the second probe set may all be the same length as each other, or they may be different lengths. The probes will have a Tm of between 65-75° C., i.e. 65, 66, 67, 68, 69, 70, 71, 72, 73, 74 or 75° C. Preferably the Tm will be 72° C.

In addition the probes may contain a non-hybridising linker region and/or a second destabilizing mutation. The probes may also comprise a locked nucleic acid (LNA) and/or a peptide nucleic acid (PNA).

As discussed above, a SNP is a DNA sequence variation occurring when a single nucleotide—A, T, C, or G—in the genome (or other shared sequence) differs across a population. SNP arrays rely on differential hybridisation to distinguish between these differences and the hybridisation probes are designed to perfectly match the different polymorphisms of the SNP. Preferably the first probe of the pair is designed to perfectly match one polymorphism and the second probe of the pair matches the second polymorphism.

Preferably the invention uses SNPs with only two alleles. More preferably the invention uses SNPs with an allelic frequency of 40-60%, e.g. 41, 42, 43, 44, 45, 46, 47, 48, 49, 50, 51, 52, 53, 54, 55, 56, 57, 58, 59 or 60%. Most preferably the SNP has an allelic frequency of 50%.

In a preferred embodiment of the invention, one of the pair of hybridisation probes is designed to perfectly match one polymorphism and the second probe is designed to perfectly match the second polymorphism. Preferably the pair of hybridisation probes is accompanied by a third and fourth probe which act as controls and correspond to the third and fourth bases respectively. For example, if the SNP has two alleles, T and G, the first probe be designed to bind to the T allele, the second probe will be designed to bind to the G allele and the third and fourth probes will be designed to bind to the same sequence containing C or A instead, thus acting as controls. The different probes for a single SNP differ in sequence from each other. If there is a single nucleotide different between two probes for a single SNP, this is preferably not at the 3' terminal nucleotide of the probes. More preferably, the probes are identical at their 3' terminal nucleotides. They may also be identical at their 5' terminal nucleotides. Thus they may differ in sequence at 1 or more internal nucleotides.

Preferably, a probe's nucleotide at the SNP position is not its 3' terminal nucleotide. More preferably a probe's nucleotide at the SNP position is not a terminal nucleotide, i.e. preferably a probe's nucleotide at the SNP position is an internal nucleotide. Preferably the two probes in a pair of hybridisation probes differ in sequence at at least one internal nucleotide.

Preferably differential hybridisation of a probe to different alleles does not arise due to a mismatch at the 3' terminal nucleotide. More preferably differential hybridisation of a probe to different alleles does not arise due to a mismatch at a terminal nucleotide i.e. preferably differential hybridisation of a probe to different alleles arises due to a mismatch at an internal nucleotide of the probe(s).

If the sample comprises a SNP which is homozygous then hybridisation of the sample will result in a signal which is higher for one of the pair of probes, i.e. the true match probe, compared to the other. A SNP which is heterozygous will give approximately the same signal for both of the pair. This is summarised in the FIG. 2. The SNPs can then be tracked to show regions of the chromosome that display Loss of heterozygosity (LOH).

LOH can be as a consequence of UPD (isodisomy) or as deletion. The integration of the array CGH data, which detects deletions in the chromosome, can be used to distinguish if LOH is caused by chromosomal deletion or isodisomy. If chromosomal deletion has not occurred and stretches of SNPs which are homozygous as opposed to heterozygous are detected, this leads to the conclusion that LOH has occurred due to isodisomy.

Preferably the second probe set will comprise multiple pair(s) of hybridisation probes for different SNP residues. For example the second probe set may comprise 10, 20, 50, 100, 250, 500, 1000, 2000, 3000, 5000, 10000, 15000 or more pairs of hybridisation probes.

Any given SNP in the human genome is represented in two complementary DNA strands: a sense strand and an antisense strand. An A base in one strand is paired with a T in the other, and a C is paired a G in the other. Thus to locate the nucleotide at any particular SNP residue it is possible to analyse either strand and to infer the complementary nucleotide. The invention can look at the sense strand or the antisense strand for any SNP. Where the invention includes two probes for differentially hybridising to two SNP targets it is usual that both of these should hybridise to the same target strand (i.e. both to the sense strand or both to the antisense strand).

The invention may not involve a step of actually determining the nucleotide at a particular SNP position, but may instead merely identify differential hybridisation to one of two probes, but this hybridisation result inherently reveals the nucleotide at the relevant position because the probes have known sequence and differentiation capability.

Preferably, hybridisation of a genomic DNA sample to a probe is not identified using a chain extension method, i.e. a method by which one or more nucleotides are added to the 3' terminal nucleotide of a probe. Preferably detection of hybridisation of genomic DNA sample to a probe is carried out without the addition of any further nucleotides to the probe. Preferably, differential hybridisation of a genomic DNA sample to probes is identified solely by observing hybridisation.

Preferably, label will not be incorporated into a probe during or after hybridisation.

Preferably the second probe set will comprise five or more hybridisation probes per chromosome, i.e., 6, 7, 8, 9, 10, 11, 12, 13, 14, 15, 16, 17, 18, 19, 20, 25, 30, 40, 50, 100, 150, 200, 250, 300 or more. The statistical significance of the results will improve with an increase number of pairs of hybridisation probes. For example, if the second probe set comprises two pairs of probes per chromosome and the test sample is shown to be homozygous for both SNPs then there is a 25% chance that the homozygosity occurred by chance. If, on the other hand, the second probe set comprises 10 pairs of probes per chromosome and the test sample is shown to be homozygous for all ten SNPs then there is a ~0.1% chance that the homozygosity occurred by chance.

The first and second probe set may comprise a different number of probes per chromosome, e.g. more, less or the same. For example the first probe set may comprise 10 pairs per chromosome and the second probe set may comprise 50. Any combination is included in the invention.

Preferably the hybridisation probes of the second probe set are between 50 to 70 nucleotides in length, i.e., 51, 52, 53, 54, 55, 56, 57, 58, 59, 60, 61, 62, 63, 64, 65, 66, 67, 68, 69 or 70. More preferably the hybridisation probes of the second probe set are 60 nucleotides in length.

The hybridisation probes on an array of the invention can be pre-synthesised before being applied to the array, or may be prepared on the array in situ (e.g. by inkjet printing, by light-directed synthesis, etc.).

The skilled person will appreciate that as the second probe set functions to track the chromosome and determine if LOH has occurred it may function as a SNP array, as described above, or may function to detect INDELs, VNTRs or transposons.

INDELs are short deletions or insertions that are only one or a few base pairs long. Instead of or in addition to targeting SNPs, the second probe set may include probes which are designed to designed to detect INDELs instead of SNPs. In this embodiment, one of the pair of hybridisation probes in the second set is designed to hybridise to DNA that contains the insertion and the second of the pair of hybridisation probesin the second set hybridises to the empty site in the DNA, or deletion. INDELs can be repetitive short insertions or deletions (more commonly known as variable numbers of tandem repeats, VNTRs, or simple sequence repeats, SSRs, or microsatellites, etc.) and so in this embodiment there may be more than one probe pair. An INDEL probe set may comprise a series of probes that are designed to hybridise to DNA containing no insertion, one, two, three or more insertions.

VNTRs are tandem repeats present in the genome. Instead of or in addition to targeting SNPs, the second probe set may comprise probes that are designed to detect VNTRs. Allelic pairs comprise VNTRs with different numbers of the repeated sequence. In this embodiment one of the set of hybridisation probes in the second set is designed to hybridise to DNA that contains one allele of the VNTR and a second of the set of hybridisation probes in the second set hybridides to DNA that contains another allele, which contains a different number of repeats. As VNTRs are variable repetitive short repeats with a range of different numbers of repeats, in this embodiment there may be more than one probe pair to represent the number of alleles in the population. A VNTR probe set may be designed such that it comprises a set of probes that are designed to hybridise to DNA containing no repeat, one, two, three or more repeats.

Transposons are movable genetic elements present in the genome. Instead of or in addition to targeting SNPs, the second probe set may comprise probes which are designed to detect transposons inserted in the genome. In this embodiment, one of the set of hybridisation probes in the second set would be designed to hybridise to DNA without the presence of the transposon. Other probes of the set of hybridisation probes in the second set would bind to DNA consisting of the transposon and the genomic DNA transposon insertion site. The chimeric probes may comprise partly of DNA complementary to the target genomic DNA and partly complementary to the transposon DNA.

The invention can be used with all such sequence variations e.g. SNPs, INDELs, VNTRs, and/or transposons (but in some places, for brevity, the text may refer only to SNPs).

Nucleic Acid Array Materials

A nucleic acid array is a plurality of hybridisation probes immobilized on a solid surface to which target nucleic nucleotide sequences can be hybridised. This format permits a sample to be contacted simultaneously with the immobilised probes in a single reaction compartment.

The preparation and use of nucleic acid arrays, and methods for analysing the hybridisation results obtained from them, are standard in the art. Preferred detection methods for analysing hybridisation results are fluorescence-based. For analysis typically specialist software which is well known in the art will be used to detect the copy number variation. For example software available from OGT, Cytosure Interpret, Agilent Genome Workbench and BlueGnome BlueFuse Multi.

As described above, the present invention combines the advantages of array CGH and SNP arrays into a single assay format and therefore provides information on copy number changes in a given subject's DNA and provides information about the nucleotide present at one or more SNP. The combination of this information allows a user to determine if LOH, if detected, has occurred as a result of isodisomy or chromosomal deletion. The SNPs (or other variations) can then be tracked to show regions of the chromosome that display LOH. LOH can be as a consequence of UPD (isodisomy) or as deletion. The integration of the array CGH data which detects deletions in the software can be used with the data obtained from the SNP probes to distinguish if LOH is caused by chromosomal deletion or isodisomy.

The hybridisation probes used in the invention are usually nucleic acid molecules. The hybridisation probes on an array will generally be at least 30 nucleotides long (e.g. >40 nt, >50 nt, >60 nt, >70 nt, >80 nt, etc.). Thus the probes may be oligonucleotides (e.g. 40-80 nucleotides long per probe), although it is also possible to use longer probes e.g. BAC DNA, PCR amplification products, etc.

The probes may be attached to the array non-covalently or, preferably, covalently.

Methods for immobilising nucleic acids onto array surfaces are well known in the art. Various methods for attaching nucleic acids to surfaces in a hybridisable format are known e.g. attachment via linkers, to a matrix on a surface, to a gel on a surface, etc. The best-known method is the photolithographic masking method used by Affymetrix for in situ synthesis of nucleotide probes on a glass surface, but electrochemical in situ synthesis methods are also known, as are inkjet deposition methods. References 9 and 10 review current methods, and also experimental designs, which are appropriate to the invention.

Bead-based arrays may be used.

The probes can be attached by a 5' terminal residue, by a 3' terminal residue, or by an internal residue. This choice may affect the detection technique and vice versa.

Various materials can be used as the solid support in arrays e.g. a plastic material or, preferably, a glass.

Hybridisation probes are typically arranged in discrete patches, and each patch can have an area of less than $10^X m^2$, where X is selected from −4, −5, −6, −7, −8, −9, −10, −11, −12, etc. Microarrays with patch sizes in the order of 10 µm×10 µm (i.e. $10^{-10} m^2$) are readily prepared using current technology. Small patches can improve detection sensitivity.

The centre-to-centre separation of patches is preferably less than $10^Y m$, where Y is selected from −2, −3, −4, −5, etc. Adjacent patches may abut or may overlap, but it is preferred that adjacent patches are separated by a gap. Overlapping patches are not preferred.

Arrays preferably contain at least $10^N$ different analytical reagents, wherein N is selected from 0, 1, 2, 3, 4, 5, 6, 7, 8 or more. Immobilisation of at least $10^6$ different oligonucleotides onto a single surface is well known in the field of microarrays. The $10^N$ different reagents will typically be arranged in $10^N$ different patches.

Where the first probe set and second probe set are arranged in discrete patches on the array these patches may be interspersed with each other, or may be on different areas of the array. For example, the discrete patches of first probe set may be arranged in a distinct area to those of the second probe set. The same is true for the pairs of the second probe set, which may be in discrete patches next to each other or arranged separately on the array. Where pairs of the second probe set also include control probes, these may be arranged in discrete patches next to the pairs or in separate areas of the array.

In preferred embodiments, the probes match regions of gDNA which substantially lack superstructure associated with condensed metaphase chromosomes from which they are derived. The general nature of the packing of DNA into eukaryotic chromosomes is well known to those of skill in the art. Briefly, the superstructure of a eukaryotic chromosome comprises many orders of complexity.

Probes for including on the array can be designed based on knowledge of the target sequences. In general, a probe will have a sequence selected such that it is specific for a single target sequence i.e. probes that can hybridise to more than one target sequence are undesirable. Specific hybridisation in this way ensures that copy number polymorphism for a particular target is directly related to the ratio obtained from the array. Given the sequences of all targets, design algorithms can select probe sequences with the required specificity.

An array of the invention may include one or more replicates of a particular immobilised nucleic acid and/or control nucleic acid e.g. duplicates, triplicates or quadruplicates. Replicates provide redundancy, provide intra-array controls, and facilitate inter-array comparisons.

Hybridisation Conditions

Preferably the hybridisation reactions of the invention are carried out using standard hybridisation buffers known in the art. Preferably the hybridisation buffer is the hybridisation buffer available from Agilent technology (Catalogue number 5188-5380).

The hybridisation reactions are preferably carried out at a temperature between 50° C. and 80° C., i.e. 50, 51, 52, 53, 54, 55, 56, 57, 58, 59, 60, 61, 62, 63, 64, 65, 66, 67, 68 69, 70, 71, 72, 73, 74, 75, 76, 77, 78, 79 or 80° C. Preferably the hybridisation reaction is carried out at about 65° C., at 65±3° C., at 65±2° C., at 65±1° C., or ideally at 65° C.

Preferably all of first probe set and second probe set can differentially hybridise to their respective nucleic acid targets under the same hybridisation conditions.

Method for Simultaneously Performing Array CGH and SNP Array Analysis

References in this section to SNPs apply equally to INDELs, VNTRs, and transposons.

As described above, the arrays of the invention are capable of simultaneously performing array CGH and SNP array analysis on a genomic DNA sample. The invention therefore provides a method for simultaneously performing array CGH and SNP array analysis on a genomic DNA sample comprising:

(a) contacting a nucleic acid array which comprises a first probe set and a second probe set with a genomic DNA sample, comprising a test and reference sample, under hybridisation conditions, wherein: (i) the first probe set, for the detection of copy number variation by array CGH, comprises a plurality of hybridisation probes substantially complementary to a plurality of target nucleotide sequences in the nucleic acid sample; and (ii) and the second probe set comprises one or more pair(s) of hybridisation probes for a SNP position, wherein the pair(s) of probes differ in sequence such that a nucleic acid target present in the sample can differentially hybridise to the two probes depending on the nucleotide at the SNP position;

(b) comparing the amount of test sample and reference sample hybridised to the hybridisation probes of the first probe set;

(c) comparing the amount of test sample and reference sample hybridised to the hybridisation probes of the second probe set; and (d) using the data obtained in steps (b) and (c) to determine the copy number of at least one locus; and at least one SNP in the genomic DNA sample.

In addition, the invention provides a method for distinguishing if loss of heterozygosity (LOH) at a locus is caused by chromosomal deletion or isodisomy comprising: (i) simultaneously performing array CGH and SNP array analysis on a genomic DNA sample according to a method of the invention; (ii) using the data obtained from step (d) of part (i) to distinguishing if loss of heterozygosity (LOH) at a locus is caused by chromosomal deletion or isodisomy; wherein, if all of the SNPs located on a particular chromosome or region of a chromosome are identified as homozygous and there is no indication of copy number variation in the same region, then it is likely that the LOH is a consequence of uniparental isodisomy; if the SNPs located in a particular chromosome or region of a chromosome are not all homozygous and there is an indication of copy number variation in that region, then it is likely that the LOH is a consequence of the chromosomal deletion and not from UPD.

The second probe set of the invention will usually comprise multiple pair(s) of hybridisation probes for different SNP residues. In the method of the invention, if all of the SNPs located on a particular chromosome or on a particular portion of a chromosome are shown to be homozygous and there is no indication from the CGH data that a chromosome deletion has occurred, then it is likely that the LOH is a consequence of UPD (isodisomy). Alternatively, if out of the SNPs located on a chromosome some are shown to be homozygous and there is an indication from the CGH data that a chromosome deletion has occurred, then it is likely that the LOH is a consequence of the chromosomal deletion and not from UPD.

Therefore, there are three possible results obtained from the assays of the invention: 1) If SNP probes indicate LOH but the array CGH probes indicate a copy number variation (CNV) then it is likely that there is a chromosomal deletion in the sample DNA; 2) if the SNPs probes indicate LOH but array CGH probes do not indicate CNV then it is likely that the sample DNA being tested contains isodisomy; and 3) if the SNP array does not indicate LOH and the array CGH probes do not indicate CNV, then it is likely that there is neither a chromosomal deletion nor isodisomy. As described above, the number of pairs of hybridisation probes in the second probe set affects the statistical significance of the data obtained.

These methods will generally look at autosomal chromosomes.

The arrays of the invention can also be used to detect heterodisomy by testing the parental DNA and the use of the SNP probes to track the parental origin of the DNA in the patient DNA.

Preferably the genomic DNA sample tested using the method of the invention is a human DNA sample.

General

The term "comprising" encompasses "including" as well as "consisting" e.g. a composition "comprising" X may consist exclusively of X or may include something additional e.g. X+Y.

The term "about" in relation to a numerical value x means, for example, x±10%. Where necessary, the term "about" can be omitted.

The word "substantially" does not exclude "completely" e.g. a composition which is "substantially free" from Y may be completely free from Y. Where necessary, the word "substantially" may be omitted from the definition of the invention.

References to "hybridisation" typically refer to specific hybridisation, and exclude non-specific hybridisation. Specific hybridisation can occur under experimental conditions chosen, using techniques well known in the art, to ensure that the majority of stable interactions between probe and target are where the probe and target have at least 90% sequence identity. The hybridisation conditions can be used to aid the design of probes in arrays, such that probe sequences are not used if they have more than 90% identity to other areas of the genome being analysed, to minimise cross-hybridisation. The stability of any particular probe/target duplex analysed depend on the buffer/washing conditions used. Stable duplexes are those that remain hybridised after washing such that they will contribute to the signal obtained for that probe when reading the array.

MODES FOR CARRYING OUT THE INVENTION

Figure 1:
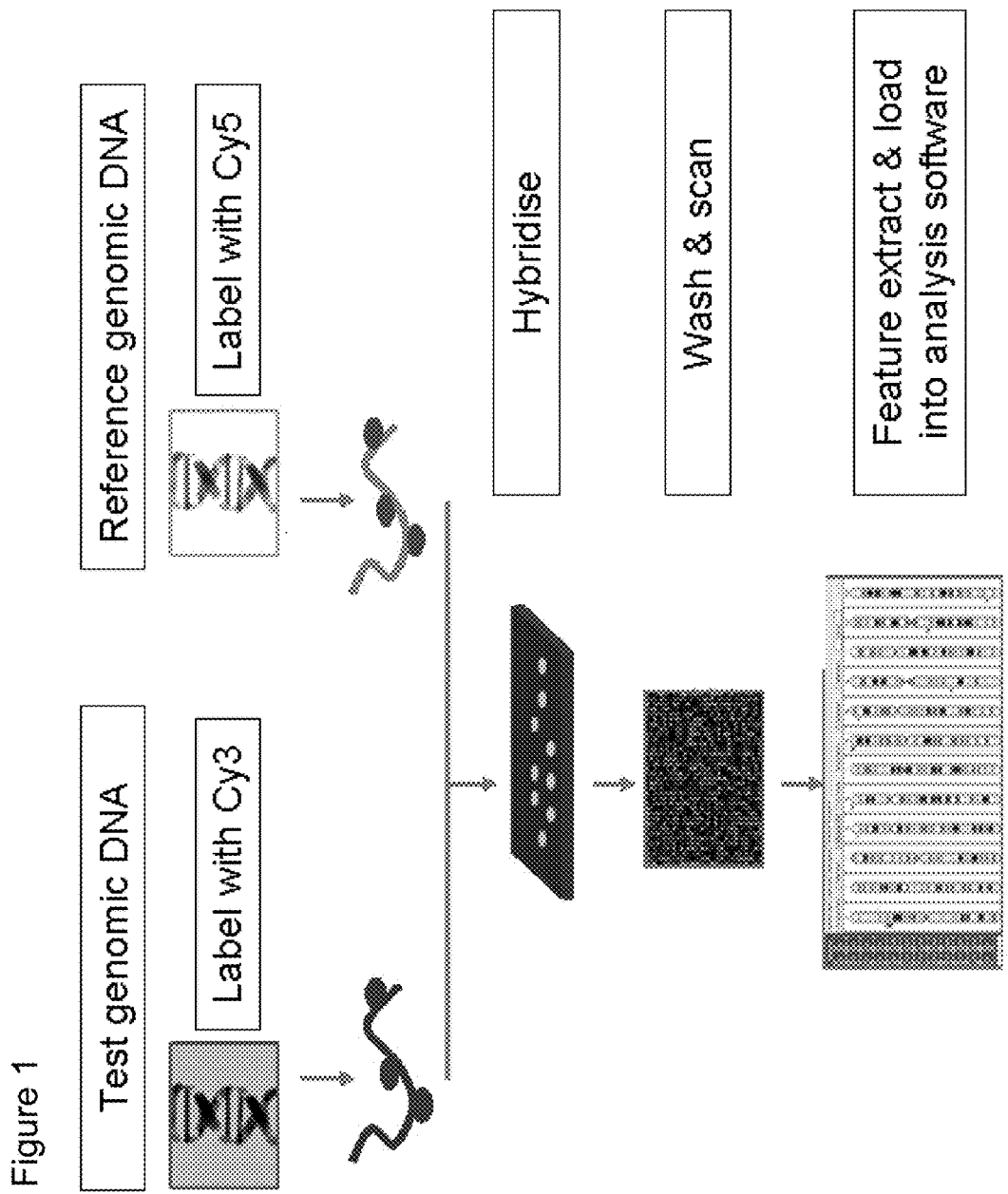
FIG. 1: Overview of array CGH.
Figure 2:
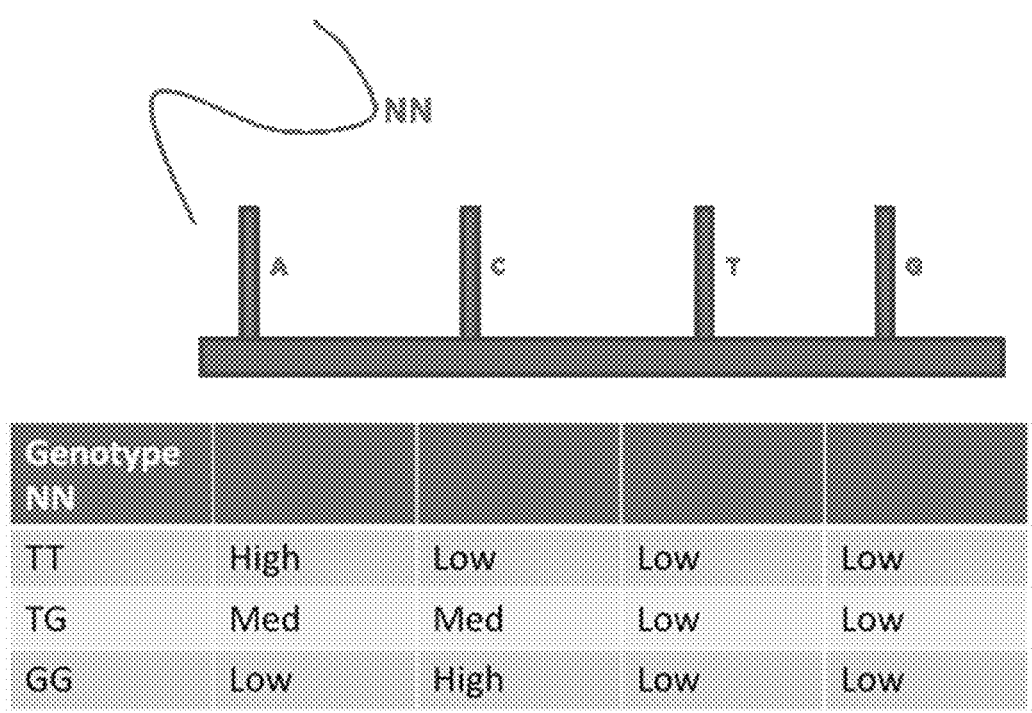
FIG. 2: Signal intensity of different probes hybridised with homozygous or heterozygous samples.

Use of SNP and CGH Probes to Detect UPD
Array Fabrication

A combined array comprising (i) ~37,116 oligonucleotide SNP probes (both allele probes, triplicate) to detect 6,186 SNPs and (ii) ~137,100 CGH probes was fabricated using ink jet in situ synthesis technology (see ref. 11) and was supplied by Agilent Technologies Inc.

Labelling

The test DNA and reference DNA were labelled using the CytoSure labelling kit (OGT catalogue number 020020). Briefly, the DNAs are digested using AluI and RsaI for 2 hours at 37° C. Following digestion and denaturation of the enzyme by heating at 65° C. for 20 mins, 10 µl random primers and 10 µl reaction buffer were added and the mix incubated at 94° C. for 3 minutes. Following 5 minutes on ice, 10 µl of nucleotide mix was pipetted into the mix. 1 µl of Cy3-dCTP was then added to the test DNA mix and 1 µl of Cy5-dCTP was added to the reference DNA mix. The reaction was started with the addition of 1 µl of exo-free Klenow and incubation at 37° C. for 2 hours. The enzyme was deactivated by incubation at 65° C. for 10 minutes.

The labelled DNA was cleaned up using CytoSure purification columns (OGT 020020). The columns were prepared by a spin at 2000 g for 1 minute. The mixes were each pipetted onto a column and the columns spun at 2000 g for 1 minute. The labelled DNA was collected.

Hybridisation

DNA was prepared for hybridisation by mixing together the labelled sample and reference DNA, then adding CotI, Blocking buffer (Agilent Technologies Inc) and 2× high rpm hybridisation buffer (Agilent Technologies Inc). The mix was denatured at 94° C. for 3 minutes, followed by incubation at 37° C. for 30 minutes. The hybridisation was set up by pipetting the mix onto an Agilent backing slide (Agilent Technologies Inc) and creating a 'sandwich' with the Microarray slide. The hybridisation was carried out using the SureHyb cassettes (Agilent Technologies Inc) and incubated at 65° C. for 40 hours at a rotation of 20 rpm in a SureHyb oven (Agilent).

Washing and Scanning

The cassettes were disassembled under aCGH Wash buffer 1 (Agilent) and the slides washed with aCGH Wash buffer 1 for 5 minutes at room temperature. A second wash was carried out in aCGH Wash buffer 2 (Agilent) for 1 minute at 37° C. The slides were scanned using an Agilent Microarray scanner at 2 μm resolution at 100% PMT setting following the manufacturer's recommendation.

Feature Extraction and Analysis

Cy3 and Cy5 intensity data from the SNP and aCGH probes was extracted from the image files using Agilent's feature extraction software.

Copy number variations (CNVs) were identified from the aCGH results by examining the ratio of the signals (Cy5/Cy3) on the CGH probes. The aberrations were then identified using a combination of Circular Binary Segmentation (CBS) and calling the segment as an aberration using two thresholds set at a value of log 2(Cy5/Cy3) exceeding 0.6 in the case of deletions and below −0.3 in the case of gains.

SNPs were genotyped by examining the ratio of the Cy3 signal on the two alleles' probes. The obtained signals were corrected using a correction factor for each individual SNP which had been ascertained from previous experiments with known genotyped samples. A threshold was then applied to call the SNP as homozygous (allele 1, AA), heterozygous (AB) or homozygous (allele 2, BB). The thresholds used were as follows: homozygous (allele 1, AA) a ratio of Cy3 signal allele 1/Cy3 signal allele 2 exceeding 0.5; heterozygous (AB) a ratio of Cy3 signal allele 1/Cy3 signal allele 2 between 0.45 and −0.45; homozygous (allele 2, BB) a ratio of Cy3 signal allele 1/Cy3 signal allele 2 below −0.5).

A small number of probes were been excluded by filtering if they failed to achieve a minimum signal or reproducibility between the 3 replicates.

Results

Detection of Isodisomy 8 UPD

Column A in Table 1 shows the number of SNPs that were homozygous on each chromosome in an Isodisomy 8 sample. Column A in Table 2 shows the position of CNVs detected using the CNV probes in the same Isodisomy 8 sample.

Figure 3:
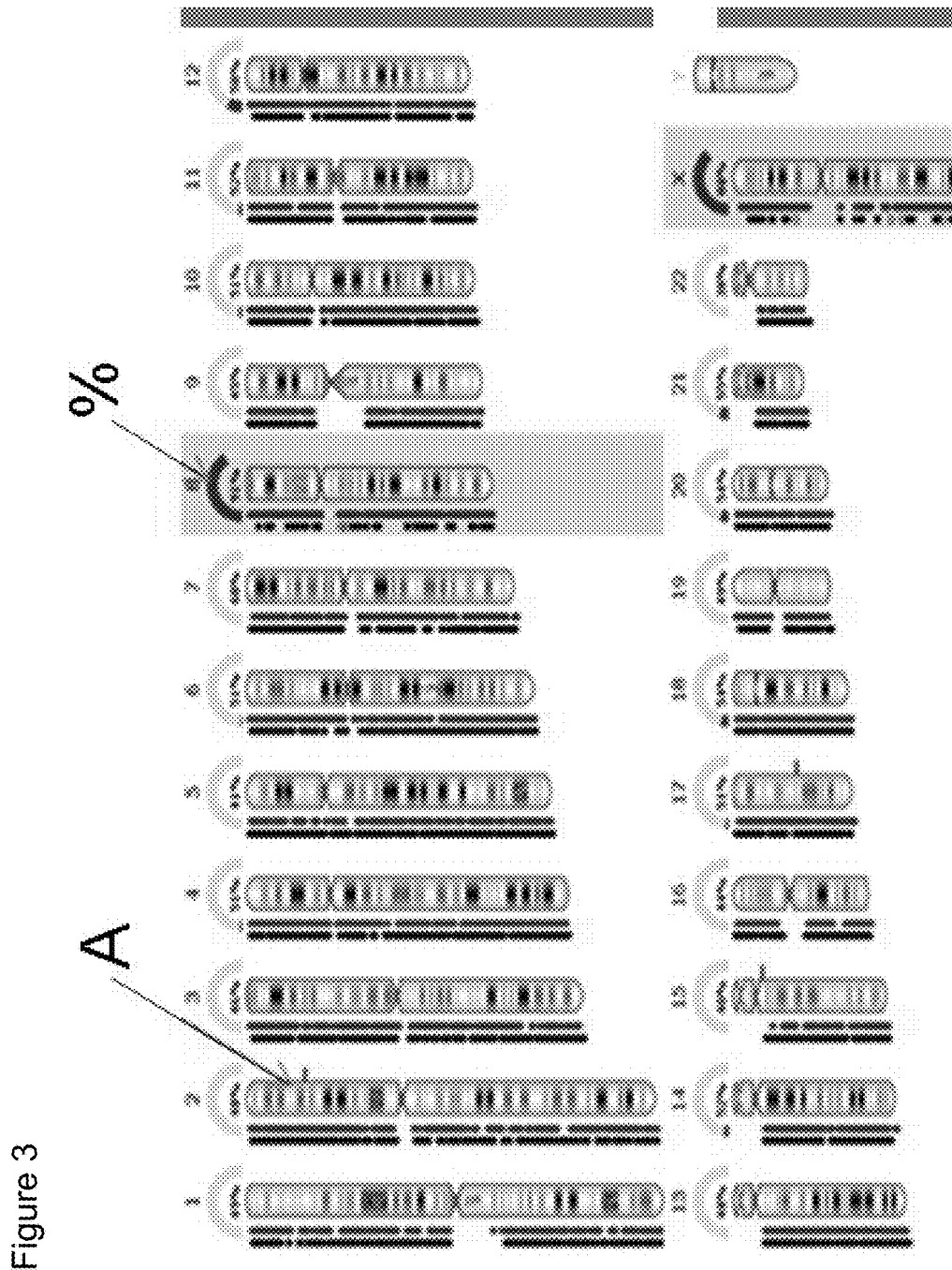
FIGS. 3 & 4: Diagrams showing an ideogram of the results from an Isodisomy 8 (FIG. 3) and an Isodisomy 15 (FIG. 4) sample using SNP and CGH probes. The arrows show an aberration (marked "A") and the % of homozygous SNPs on a chromosome ("%"), which is indicated as a dark shading on a semicircular annulus.

Most chromosomes have 50±2% of their SNPs that are homozygous. All chromosomes except for Chromosome 8 and X have between 38%-58% of their SNPs that are homozygous. 91% of SNPs on chromosome 8 are homozygous, which indicates that the arrays have detected a significant loss of heterozygosity (LOH) at chromosome 8. The CNV probes have not detected a large deletion on chromosome 8, so this indicates that the LOH is due to isodisomy 8. The X chromosome also indicates a LOH on chromosome X. This is because the sample is a male sample and therefore contains a single X chromosome. The reference used was male. FIG. 3 shows an ideogram with the results of the SNP probes and the CNV probes.

Detection of Isodisomy 15 UPD

Column B in Table 1 shows the number of SNPs that were homozygous on each chromosome in an Isodisomy 15 sample. Column B in Table 2 shows the position of CNVs detected using the CNV probes in the same Isodisomy 15 sample.

Most chromosomes have 50±2% of their SNPs that are homozygous. All chromosomes except for chromosome 15 and X have between 42-58% of SNPs that are homozygous.

Figure 4:
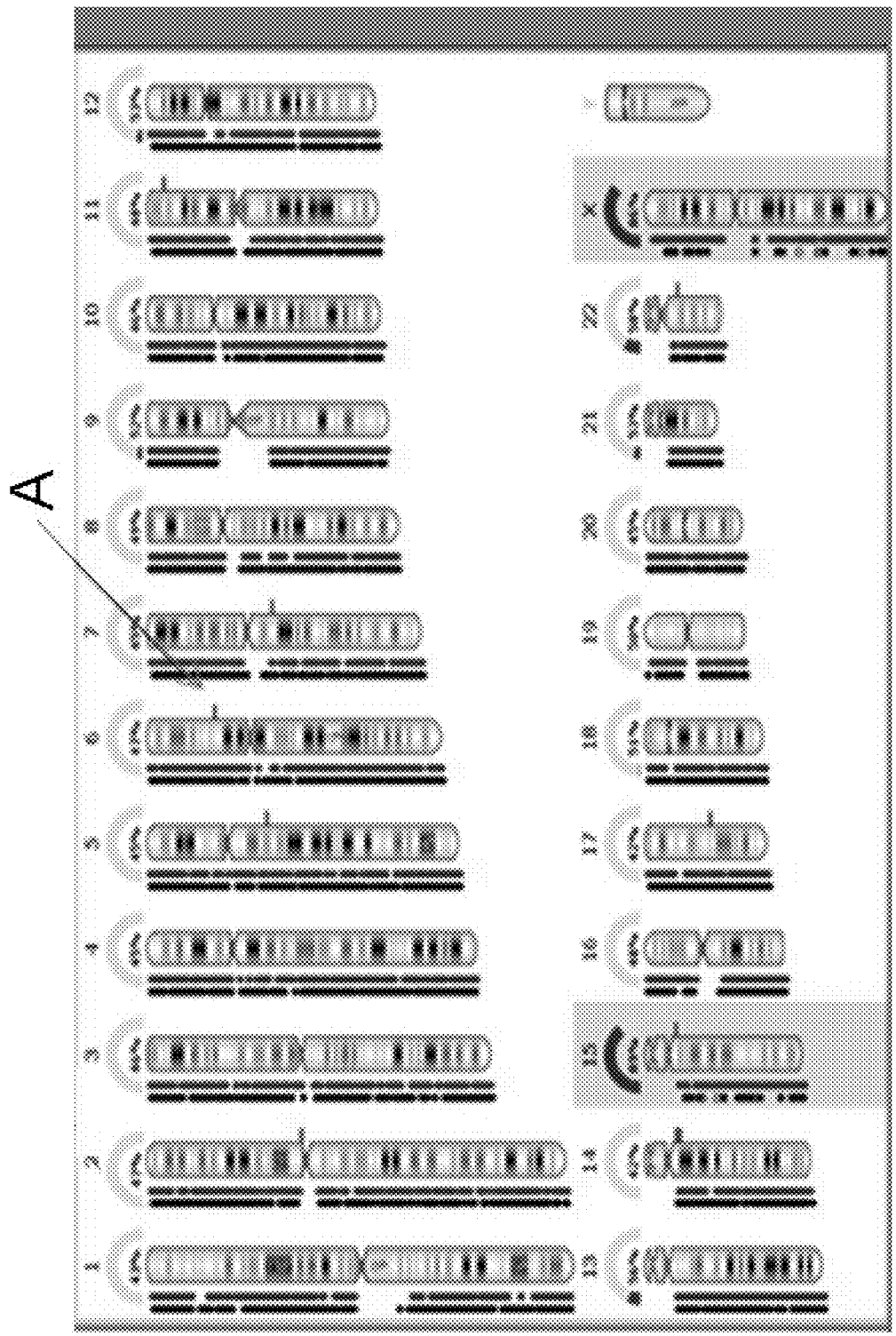

89% of SNPs on chromosome 15 are homozygous, indicating a significant LOH on chromosome 15. Examination of the CNV probes detected no aberrations (by examining the ratio of sample signal/reference signal). Therefore this suggests that the LOH was not due to a deletion and was due to isodisomy on chromosome 15. The other chromosome indicating LOH was chromosome X. This is because the sample is a male sample and therefore contains a single X chromosome. The reference used was male. FIG. 4 shows an ideogram with the results of the SNP probes and the CNV probes.

Use of Indel and CGH Probes to Detect UPD

Array Fabrication

A combined array comprising oligonucleotide indel probes (both allele probes, in triplicate) to detect 490 indels and ~43,323 CGH probes was fabricated using ink jet in situ synthesis as described above. Note more than one probe type may be used to detect each indel.

Labelling

The test DNA and reference DNA were labelled using the CytoSure labelling kit (OGT 020020). Briefly, the DNAs are denatured for 20 mins with 10 μl random primers and 10 μl reaction buffer at 99° C. for 20 mins. Following 5 mins on ice 10 μl of nucleotide mix was pipetted into the mix. 10 μl of Cy3-dCTP was then added to the test DNA mix and 10 μl of Cy5-dCTP was added to the reference DNA mix. The reaction was started with the addition of 10 μl of exo-free Klenow and incubation at 37° C. for 2 hours. The enzyme was deactivated by incubation at 65° C. for 10 minutes.

Labelled DNA was cleaned up using CytoSure purification columns, as described above.

Hybridisation, Washing and Scanning

Hybridisation, washing and scanning was performed for the indel/CGH arrays in the same way as described above for the SNP/CGH arrays.

Feature Extraction and Analysis

Cy3 and Cy5 intensity data from the Indel and aCGH probes were extracted and normalised from the image files in the same way as described above for the SNP/CGH arrays. CNVs were identified from the aCGH results in the same way. Indels were genotyped by examining the ratio of the Cy3 signal on the two alleles' probes in the same way as described above for SNP genotyping.

Results

Detection of Isodisomy 8 UPD

Column C in Table 1 shows the number of indels that were called homozygous on each chromosome in an known whole chromosome 8 isodisomy sample. Column C in Table 2 shows the position of CNVs detected using CNV probes in the same isodisomy 8 sample.

Figure 5:
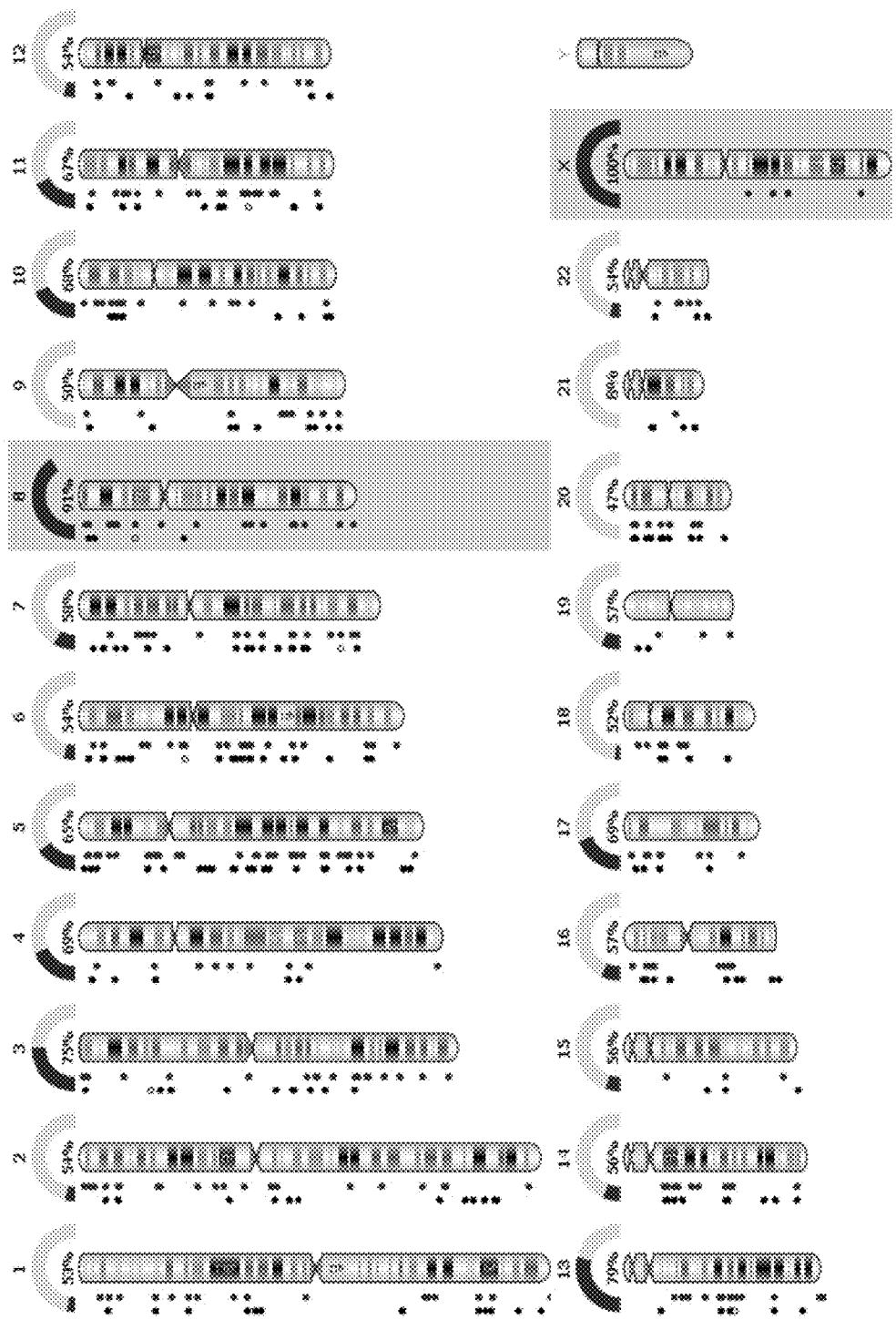
FIGS. 5 & 6: Diagrams showing an ideogram of the results from an Isodisomy 8 (FIG. 5) and an Isodisomy 15 (FIG. 6) sample using indel probes.

Most chromosomes have 50±10% of their indels that are homozygous. The low figure for chromosome 21 is likely due to incomplete coverage of this chromosome by indel probes. The number of homozygous indels on chromosome 8 is 91%, which indicates that the arrays have detected a significant LOH at chromosome 8. The CNV probes have not detected a large deletion on chromosome 8, so this indicates that the LOH is due to isodisomy 8. The X chromosome also indicates a LOH on chromosome X. This is because the sample is a male sample and therefore contains a single X chromosome. The reference used was male. FIG. 5 shows an ideogram with the results of the indel probes.

Detection of Isodisomy 15 UPD

Column D in Table 1 shows the number of indels that were homozygous on each chromosome in an Isodisomy 15 sample. Column D in Table 2 shows the position of CNVs detected using the CNV probes in the same isodisomy 15 sample.

Figure 6:
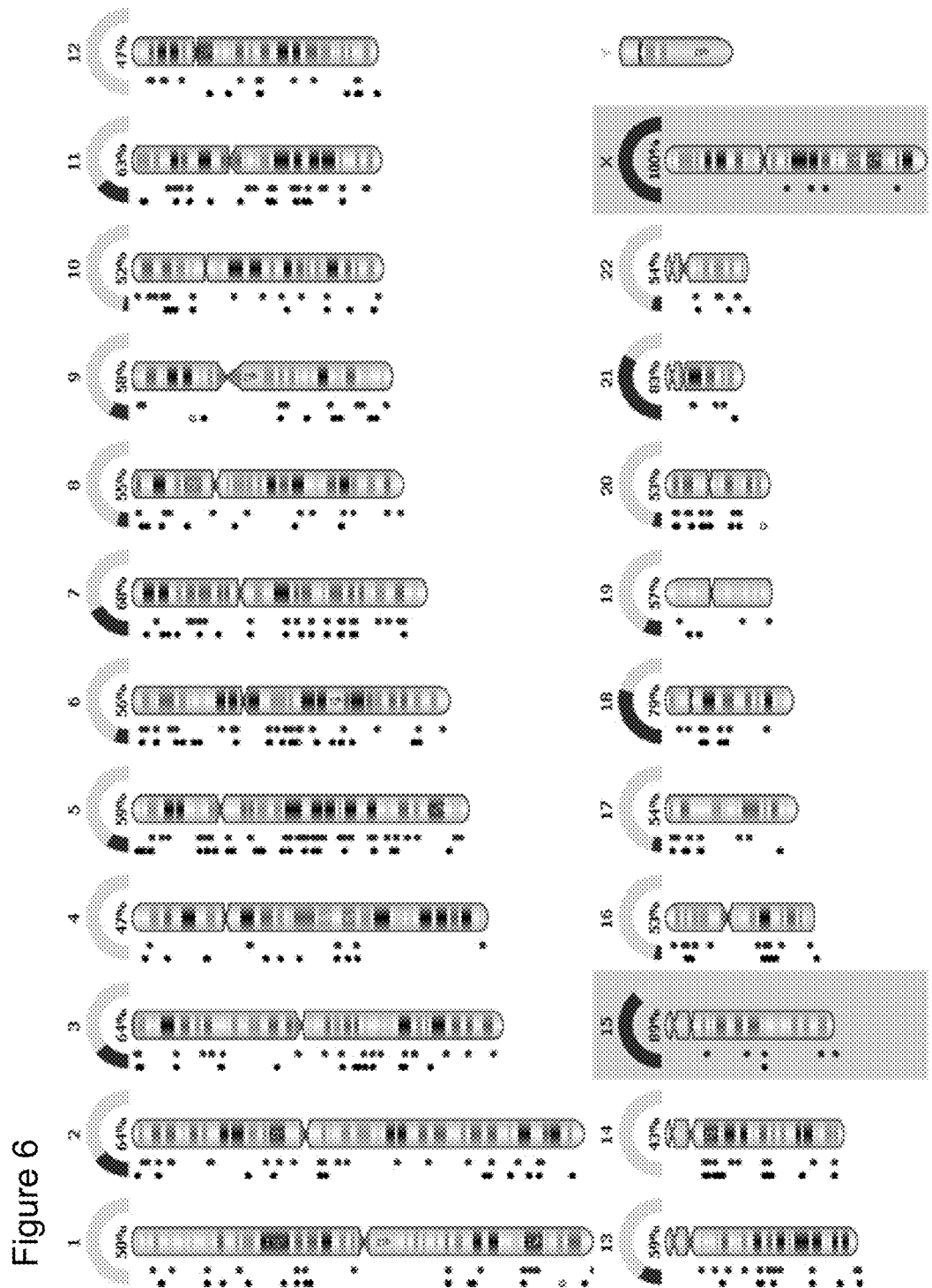

Most chromosomes have 50±10% of their indels that are homozygous. All chromosomes except for chromosome 15, 18, 21 and X have between 43-68% of indels that are homozygous. 89% of chromosome 15 indels are homozygous, indicating a significant LOH on chromosome 15. The high figures for chromosomes 18 and 21 are likely due to the low number of indels on these chromosomes (24 and 12 respectively). Examination of the CNV probes on chromosome 15 detected no aberrations (by examining the ratio of sample signal/reference signal). Therefore this suggests that the LOH was not due to a deletion and was due to isodisomy on chromosome 15. The other chromosome indicating LOH was chromosome X. This is because the sample is a male sample and therefore contains a single X chromosome. The reference used was male. FIG. 6 shows an ideogram with the results of the indel probes.

Use of VNTRs and CGH Probes to Detect UPD

Array Fabrication

One VNTR probe on chromosome 8 appeared to perform adequately in test experiments. This probe bound to the VNTR designated r58192897 by dbSNP. A combined array comprising this VNTR probe (both alleles in triplicate) and ~15,159 CGH probes was fabricated using ink jet in situ synthesis technology as described above.

Labelling

The test DNA and reference DNA were labelled using the CytoSure labelling kit (OGT 020020). Briefly, the DNAs are denatured for 20 mins with 10 μl random primers and 10 μl reaction buffer at 99° C. for 20 mins. Following 5 mins on ice 10 μl of nucleotide mix was pipetted into the mix. 10 μl of Cy3-dCTP was then added to the test DNA mix and 10 μl of Cy5dCTP was added to the reference DNA mix. The reaction was started with the addition of 1 μl of exo-free Klenow and incubation at 37° C. for 2 hours. The enzyme was deactivated by incubation at 65° C. for 10 minutes.

Subsequent steps of (i) cleaning labelled DNA, (ii) hybridisation, (iii) washing, (iv) scanning, (v) feature extraction, and (vi) data analysis were all performed in the same way as described above for the SNP and indel arrays. VNTRs were genotyped by examining the ratio of the Cy3 signal on the two alleles' probes in the same way as described above for and SNP and indel genotyping.

Detection of Isodisomy 8 UPD

The CGH probes indicate that there is no large deletion on chromosome 8, and the VNTR probe calls its allele as homozygous. A single CNV was detected using the CGH probes, namely a 0.79 Mb loss on chromosome 14. As there is no large CNV detected on chromosome 8 the homozygous call for the VNTR probe indicates that the combination of VNTR probes and aCGH probes can be used to identify UPD.

It will be understood that the invention has been described by way of example only and modification of detail may be made without departing from the spirit and scope of the invention.

TABLE 1

% of SNPs on indicated chromosome which are homozygous

| Chromosome | A | B | C | D |
|---|---|---|---|---|
| 1 | 49% | 43% | 53% | 50% |
| 2 | 48% | 47% | 54% | 64% |
| 3 | 46% | 46% | 75% | 64% |
| 4 | 51% | 45% | 69% | 47% |
| 5 | 41% | 45% | 65% | 59% |
| 6 | 51% | 47% | 54% | 56% |
| 7 | 48% | 45% | 58% | 68% |
| 8 | 91% | 49% | 91% | 55% |
| 9 | 45% | 52% | 50% | 58% |
| 10 | 51% | 46% | 68% | 52% |
| 11 | 52% | 48% | 67% | 63% |
| 12 | 58% | 53% | 54% | 47% |
| 13 | 48% | 56% | 79% | 59% |

TABLE 1-continued

% of SNPs on indicated chromosome which are homozygous

| Chromosome | A | B | C | D |
|---|---|---|---|---|
| 14 | 52% | 42% | 56% | 43% |
| 15 | 40% | 89% | 56% | 89% |
| 16 | 44% | 48% | 57% | 53% |
| 17 | 51% | 42% | 69% | 54% |
| 18 | 54% | 51% | 52% | 79% |
| 19 | 49% | 50% | 57% | 57% |
| 20 | 54% | 45% | 47% | 53% |
| 21 | 55% | 53% | 8% | 83% |
| 22 | 38% | 58% | 54% | 54% |
| X | 88% | 86% | 100% | 100% |

TABLE 2

Aberrations detected by CNV probes (exceeding 0.25 Mb)
Only those CNVs exceeding 0.25 Mb are shown

| Chromosome | A | B | C | D |
|---|---|---|---|---|
| 1 | | | | |
| 2 | Loss 0.27 Mb | 0.94 Mb loss | | 1.5 Mb gain |
| 3 | | | | |
| 4 | | | 1.17 Mb loss | 2.23 Mb gain |
| 5 | | 2.02 Mb gain | | 1.34 Mb gain |
| 6 | | 0.28 Mb gain | | |
| 7 | | 0.3 Mb gain | | |
| 8 | | | | 1.75 Mb, 0.52 Mb, 1.16 Mb gain |
| 9 | | | | |
| 10 | | | | |
| 11 | | 0.48 Mb gain | | 0.39 Mb gain |
| 12 | | | | 2.95 Mb gain |
| 13 | | | | |
| 14 | | 0.34 Mb gain, 0.32 Mb gain | | 0.67 Mb gain, 1.49 Mb gain |
| 15 | Gain 0.75 Mb | 0.31 Mb gain | Gain 0.75 Mb | |
| 16 | | | | |
| 17 | Loss 0.47 Mb | 0.36 Mb gain | Loss 0.47 Mb | |
| 18 | | | | |
| 19 | | | | |
| 20 | | | | |
| 21 | | | | |
| 22 | | 0.69 Mb loss | | 0.65 Mb loss, 1.75 Mb gain |
| X | | | | |

REFERENCES

[1] WO93/18186.
[2] WO96/17958.
[3] Oostlander et al. 92004) Clin Genet 66:488-95.
[4] Pinkel et al. (1998) Nature Genet 20:207-11.
[5] Robinson W P (2000). Bioessays 22 (5): 452-9.
[6] Kloth et al. (2007) BMC Genomics 8:53 doi:10.1186/1471-2164-8-53.
[7] US 2007/0238106.
[8] Lage et al. (2003) Genome Res 13:294-307.
[9] Nakaya et al. (2007) pages 265-307 of *Nucleic Acid Hybridisation* ISBN 1402060394.
[10] Matson (2009) *Microarray Methods and Protocols.* CRC Press. ISBN 1420046659.
[11] Hughes et al (2001) Nature Biotechnol 19(4):342-7.

The invention claimed is:

1. A method for distinguishing if loss of heterozygosity (LOH) at a locus is caused by chromosomal deletion or isodisomy comprising:
   (A) simultaneously performing array CGH and SNP array analysis; array CGH and INDEL array analysis; array CGH and VNTR array analysis; or array CGH and transposon array analysis on a genomic DNA sample comprising steps (a) to (d):
      (a) contacting a nucleic acid array which comprises a first probe set and a second probe set with a genomic DNA sample, comprising a test and reference sample, under hybridisation conditions, wherein:
         (i) the first probe set, for the detection of copy number variation by array CGH, comprises a plurality of hybridisation probes substantially complementary to a plurality of target nucleotide sequences in the nucleic acid sample; and
         (ii) the second probe set comprises one or more pair(s) of hybridisation probes comprising a first allele probe and a second allele probe, wherein the probes are 50-70 nucleotides in length comprising a linker sequence of up to 30 nucleotides in length for one or more of
            a SNP position
            an INDEL position
            a VNTR position
            a transposon position
            wherein the pair(s) of probes differ in sequence such that a nucleic acid target present in the sample can differentially hybridise to the two probes depending on
            the nucleotide at the SNP position,
            the sequence at the INDEL position
            the number of tandem repeats at the VNTR position
            the presence or absence of a transposon at the transposon position wherein a probe's nucleotide at the SNP position is not its 3' terminal nucleotide;
      (b) comparing the amount of test sample and reference sample hybridised to the hybridisation probes of the first probe set;
      (c) comparing the amount of test sample hybridized to the first allele probe and the second allele probe of the second probe set; and
      (d) using the data obtained in steps (b) and (c) to determine both the copy number of at least one locus and one or more of
         at least one SNP in the genomic DNA sample
         at least one INDEL in the genomic DNA sample
         at least one VNTR in the genomic DNA sample
         at least one transposon in the genomic sample
   (B) using the data obtained from step (d) of part (A) to distinguish if loss of heterozygosity (LOH) at a locus is caused by chromosomal deletion or isodisomy;
      wherein, if substantially all of the SNPs, INDELs, VNTR, or transposons located on a particular chromosome or region of a chromosome are identified as homozygous and there is no indication of copy number variation in the same region, then it is likely that the LOH is a consequence of uniparental isodisomy; if the SNPs, INDELs, VNTR, or transposons located in a particular chromosome or region of a chromosome are not all homozygous and there is an indication of copy number variation in that region, then it is likely that the LOH is a consequence of the chromosomal deletion and not from uniparental isodisomy; and
      wherein the test and reference samples present in the genomic DNA sample are each labelled with a label distinguishable from each other.

2. A nucleic acid array that, when contacted with a genomic DNA sample under hybridisation conditions can:
   (a) provide information about the sample relating to the copy number of one or more loci in the genome; and
   (b) distinguish between different alleles present at one or more SNP, INDEL, VNTR or transposon position,
   comprising a first probe set and a second probe set, wherein:
      (i) the first probe set, for the detection of copy number variation by array CGH, comprises a plurality of hybridisation probes substantially complementary to a plurality of target nucleotide sequences in the nucleic acid sample; and
      (ii) the second probe set comprises one or more pair(s) of hybridisation probes for a SNP, INDEL, VNTR or transposon position, wherein the pair(s) of probes differ in sequence such that a nucleic acid target present in the sample can differentially hybridise to the two probes depending on the nucleotide at the SNP INDEL, VNTR or transposon position; wherein a probe's nucleotide at the SNP position is not its 3' terminal nucleotide; and
   wherein the first probe set and the second probe set are present together on a single array.

3. The nucleic acid array according to claim 2, wherein the probes of the first probe set are each greater than 60 nucleotides long.

4. The nucleic acid array according to claim 2, wherein the one or more pair(s) of the second probe set are each 60 nucleotides long.

5. The nucleic acid array according to claim 2, wherein the first and second probe set are DNA.

6. The nucleic acid array according to claim 2, wherein the SNP residue has an allelic frequency between 40%-60%.

* * * * *